United States Patent [19]
Shillington

[11] Patent Number: 5,693,028
[45] Date of Patent: Dec. 2, 1997

[54] ONE HAND NEEDLE RELEASE SYSTEM

[75] Inventor: Richard A. Shillington, Bonsall, Calif.

[73] Assignee: Med-Safe Systems, Inc., Oceanside, Calif.

[21] Appl. No.: 483,306

[22] Filed: Jun. 7, 1995

Related U.S. Application Data

[63] Continuation-in-part of Ser. No. 370,241, Jan. 9, 1995.

[51] Int. Cl.[6] .................................................. A61M 5/00
[52] U.S. Cl. ........................... 604/240; 604/187; 604/242
[58] Field of Search .................................... 604/110, 187, 604/192, 197, 198, 205, 206, 218, 240, 241, 242, 263, 411, 414, 232

[56] References Cited

U.S. PATENT DOCUMENTS

| | | | |
|---|---|---|---|
| 1,683,350 | 9/1928 | Hein . | |
| 3,063,450 | 11/1962 | Myerson et al. | 128/218 |
| 4,490,142 | 12/1984 | Silvern | 604/241 |
| 4,768,568 | 9/1988 | Fournier et al. | 141/286 |
| 5,000,744 | 3/1991 | Hoffman et al. | 604/232 |
| 5,002,537 | 3/1991 | Hoffman et al. | 604/232 |
| 5,062,837 | 11/1991 | Al-Sioufi et al. | 604/240 |
| 5,217,025 | 6/1993 | Okamura | 128/765 |

*Primary Examiner*—Michael Powell Buiz
*Assistant Examiner*—Cris L. Rodriguez
*Attorney, Agent, or Firm*—Baker, Maxham, Jester & Meador

[57] ABSTRACT

A quick release needle holder, comprises a tubular barrel having a needle receiving socket on one end, the needle receiving socket having a segmented wall defining a plurality of annular jaws having internal threads, a device for normally biasing the jaws into an inner position for threadably receiving a needle hub, and a device having finger tabs slideably mounted on the holder for releaseably biasing the jaws to a needle hub releasing position.

20 Claims, 1 Drawing Sheet

ONE HAND NEEDLE RELEASE SYSTEM

REFERENCE TO RELATED APPLICATIONS

The present application is a continuation-in-part of co-pending application Ser. No. 08/370,241, filed Jan. 9, 1995, and entitled "QUICK RELEASE NEEDLE REMOVAL APPARATUS".

BACKGROUND OF THE INVENTION

The present invention relates to needle removal devices for syringes and other needle holders and pertains particularly to an improved needle release apparatus for quick and easy one hand removal of needles from holders.

A huge volume of hypodermic needles are used daily in the medical and health care industry and must be disposed of safely. These used needles pose a major health problem to the medical personnel using them as well as others who may come into contact with them either innocently or deliberately. The safe and effective disposal of these hypodermic needles poses one of the greatest disposal problems for the medical and health care industry.

Hypodermic needles are widely used for both injection of medication and for withdrawing blood samples for diagnostic purposes. In many instances the needle is removed from the holder and disposed of separately from the holder. In some cases, particularly with certain blood drawing or collection devices, the holder may be reused. In these cases, it is essential that the needle be easily, quickly and safely removed and disposed of without risk to the user.

The typical hypodermic needle comprises an elongated thin cannula having a sharp tip on one end and a hub at or near the other end for detachable attachment to a tubular holder such as a syringe or collector. The hub may have a threaded screw connector, Luer lock, or other type connector. The needle is usually covered with a protective tube or sheath detachably coupled to the hub for hand manipulation to aid in connecting the needle to the holder. The protective sheath is removed after the needle is mounted in the holder and when it is to be used. The sheath may be again used to protectively cover the needle after use. However, attempts to reinsert the needle into the sheath often result in pricks of the skin of the user. Therefore, direct disposal into a sharps container following use is desirable.

The present common technique of drawing blood samples is by means of an evacuated tube and holder combination such as that sold under the trademark VACUTAINER by the Becton Dickinson Company. These blood collection assemblies comprise a tubular holder or barrel having an open end to receive an evacuated collection tube and a double needle in the other end. The needle is threadably mounted in one end of the tubular holder with an exterior needle for penetrating the patient tissue for receiving blood. The interior needle is covered with a sheath valve and penetrates an elastomeric stopper in one end of an evacuated vacuum tube which acts to draw the blood.

Many devices have been proposed in the past for removal and disposal of the needles. Examples of these are disclosed in the following U.S. patents:

Shillington U.S. Pat. No. 4,667,821
Shillington U.S. Pat. No. 4,984,686
Thead et al. U.S. Pat. No. 4,986,811
Sagstetter et al. U.S. Pat. No. 5,086,922
Sagstetter et al. U.S. Pat. No. 5,092,462
Shillington U.S. Pat. No. 5,249,680

These prior art devices are generally effective to remove the needles. However, they all have various drawbacks. For example, many of them cannot be effectively used with one hand and require the use of both hands. This is usually difficult or inconvenient for the user.

In the above identified parent application, we disclose a needle holder apparatus having means for releasing the needle from the holder when it is inserted into a special opening in a container and pressed forward. That holder required a special opening in the container for engagement with the forward end of the holder.

It is desirable that a simple, safe and effective quick release needle holder for hypodermic needles be available that can be used with one hand without special tools or containers.

SUMMARY OF THE INVENTION

It is the primary object of the present invention to provide a simple and effective quick one hand release needle holder for hypodermic needles.

In accordance with a primary aspect of the present invention, a quick release needle holder for hypodermic needles, comprises a tubular barrel having a needle hub receiving socket on one end, said needle receiving socket having a segmented wall defining a plurality of inwardly directed annular jaws for receiving and gripping a needle hub, means for normally biasing said jaws inwardly to an innermost position for gripping and mounting a needle hub, and finger operable means for releasably biasing said jaws to a needle hub releasing position.

BRIEF DESCRIPTION OF THE PREFERRED EMBODIMENTS

The above and other objects and advantages of the present invention will become apparent from the following description when read in conjunction with the accompanying drawings wherein.

Figure 1:
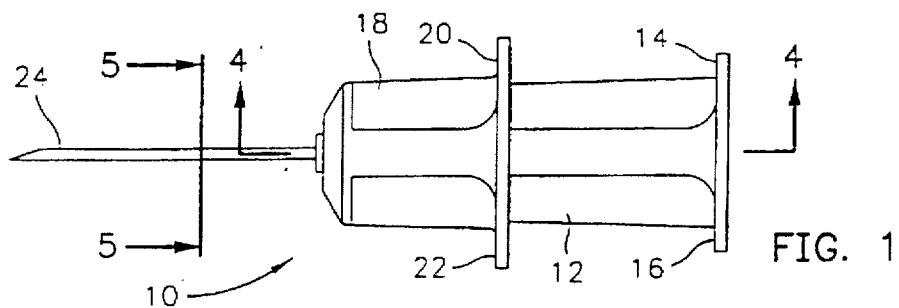
FIG. 1 is a side elevation view of a preferred embodiment of the invention.
Figure 4:
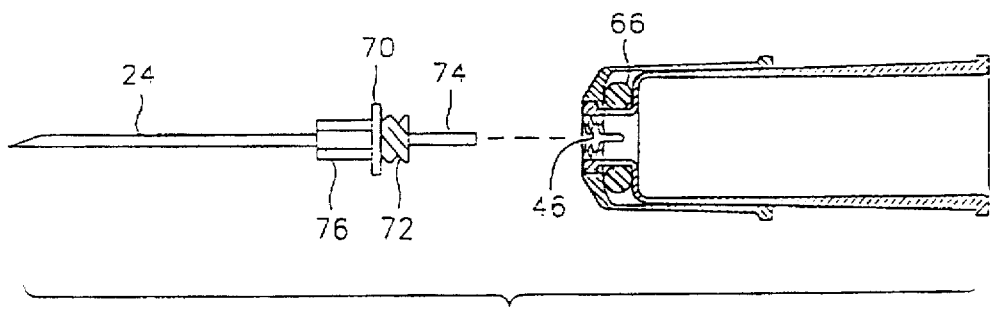

FIG. 4 section view taken generally on line 4—4 of FIG. 1; and

Figure 3:
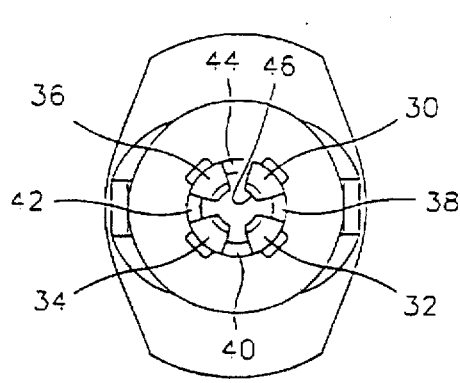
FIG. 3 is a view taken generally on line 3—3 of FIG. 2.
Figure 5:
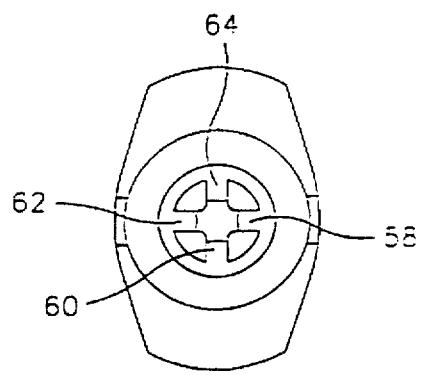

FIG. 5 is a view like FIG. 3 taken generally on line 5—5 of FIG. 1 with the needle omitted.

DETAILED DESCRIPTION OF THE PREFERRED EMBODIMENTS

Figure 2:
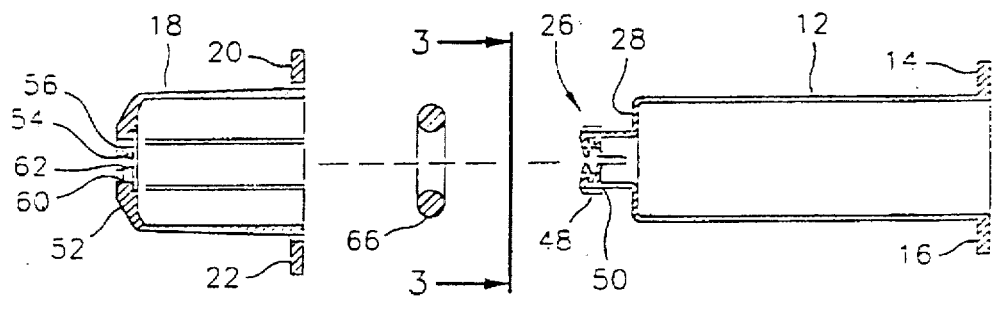
FIG. 2 is a an exploded assembly view in section of the embodiment of FIG. 1.

Referring to FIGS. 1 and 2 of the drawings an exemplary embodiment of the invention embodied in a holder of a blood collection assembly is illustrated and designated generally by the numeral 10. The blood collection assembly comprises an elongated generally cylindrical tube or barrel 12 having finger flanges 14 and 16 extending outward from opposite sides at a back open end thereof. A release sleeve 18 is reciprocally mounted on the forward end of the barrel 12 and includes finger flanges 20 and 22 extending outward from opposite sides of the rear end thereof. A needle 24 is threadably mounted in a forward axially extending neck portion defining a needle hub mounting socket designated generally by the numeral 26 on the forward end of the barrel. The present invention was devised specifically for blood collection assemblies but is applicable to other hypodermic needle holders such as syringes, IV tubing site connectors and the like.

As best illustrated in FIGS. 2, 3 and 4, the tube or barrel has a forward end-wall 28 with the reduced needle hub mounting socket 26 formed of a reduced forwardly projecting neck or annular wall portion that is segmented into four segments or jaws 30, 32, 34 and 36. These segments are defined by axially extending full length slots 38, 40, 42 and 44. The segments 30–36 define a plurality of inwardly directed annular jaw members having internal threaded surfaces 46 which form a socket for threadably receiving and mounting a needle hub. The jaw members are formed with internal threads 46 for threadably receiving the threaded needle hub 72 of a needle 24. Other forms of needle connectors may also be used.

The jaws 30–36 extend coaxially and are annularly spaced about the central longitudinally axis of the barrel 12. The jaws or segments of the hub are further mounted to pivot inwardly and outwardly toward and away from the central axis for gripping and releasing a threaded hub of a needle, respectively. The barrel 12 is preferably fabricated from a polycarbonate compound and has some spring characteristics to enable the hub segments to be biased outward to release a needle hub 72. The hub segments are formed to be normally biased to the innermost position to threadably receive a needle hub 72. Each segment is also formed with an outer protrusion 48 forming an undercut or retainer shoulder 50.

The longitudinally slidable releasing sleeve 18 is formed with a forward wall 52 having an aperture 54 with an annular shoulder 56 for engaging retainer shoulders 50 behind protrusions 48 (FIG. 2). This retains the sleeve 18 in place on the neck of the needle mounting socket 26. The aperture 54 is formed by an annular wall or shoulder that engages the outer surface of the jaws and normally biases them inward to an innermost position. Also formed in the aperture 54 of the forward end wall 52 are a plurality of inwardly projecting wedges 58, 60, 62, and 64 (FIG. 5) which extend in the slots 38, 40, 42 and 44 for biasing or camming the segments or jaws apart as the sleeve 18 is pulled or slid backward toward the rear or back end of the tube 12. This action of sliding the sleeve 18 backward on the tube 12 biases or cams the jaws 30–34 apart releasing the needle hub allowing it to drop from the socket 26. The wedge members 58–64 act as cam means for camming engagement with surfaces of the slots between the jaw members for biasing them outwardly into a needle hub releasing position. The sleeve is normally biased to a forwardmost position by an elastic collar 66, as shown in FIGS. 2 and 4 for retaining the jaws in an innermost position for threading engagement with the hub of the needle. The elastic collar 66 is captured between the end wall 28 of tube 12 and the inner surface of end wall 52 of the slidable sleeve 18.

The connector assembly is designed to threadably receive or grip the threaded hub 72 of a needle 24 of the type as shown in FIG. 4. The sleeve 18 is normally biased to the forwardmost position by means of a silicone collar or spring 66 so that the jaws can threadably receive the hub of the needle. The sleeve may be biased to the rearmost position by engaging the finger flanges 20 and 22 with the fore-finger and second finger and engaging the rear of tube 12 with the thumb, pressing the fingers and thumb toward one another slides the sleeve 18 along tube 12 camming the jaws open and releasing the hub of the needle.

Referring to FIG. 4 the needle connector assembly is designed to mount and retain a conventional needle assembly of the type designed for blood collection holders as illustrated. The needle 24 is an elongated hollow cannula having a threaded hub which comprises a central radially extending disk like flange 70 with a threaded stud like member 72 and an internal needle 74 extending therefrom. A splined or fluted coupling 76 is formed on the forward end of the needle assembly comprising axially elongated radially extending splines or ribs. The needle assembly has an outer or external needle 24 and an inner or internal needle 74 which is covered by a silicone sheath that forms or acts as a valve.

The needle is mounted in the retainer and connector assembly of the tube 12 by threadably extending the needle hub assembly into the socket 26. The needle flange 70 engages the outer ends of the jaws and stops or positions the threaded portion 72. The forward bias of the sleeve by the spring force of the collar 66 forces or maintains the jaws to their inner or inward gripping position for gripping or threadably receiving the hub of the needle assembly. This positions the inner needle inside the tube 12 to be engaged and to puncture a stopper of a vacuum blood collection tube.

When it is desired to remove the needle, the sleeve is simply moved backward on the tube 12 biasing the jaws open releasing the needle hub for its removal. This is accomplished by pressing forward on the back end of the sleeve while pulling backward on the finger tabs or flanges 20 and 22 on the sleeve while holding it over a container so that the needle is quickly released and falls directly into a disposable container.

While I have illustrated my invention by means of specific embodiments, it is to be understood that numerous changes and modifications may be made therein without departing from the spirit and scope of the invention, as defined in the appended claims.

I claim:

1. A quick release needle holder for hypodermic needles, comprising:

a tubular barrel having a longitudinal axis and a needle hub receiving socket formed integral therewith on one end;

said needle receiving socket having a segmented wall defining a plurality of inwardly directed annular jaws having a forward end;

biasing means including an annular shoulder mounted for axial movement on said jaws and including elastic means normally biasing said annular shoulder toward said forward end and said jaws inwardly to an innermost position for receiving and mounting a needle hub; and said biasing means including finger operable releasing means slideably mounted on said barrel and moveable away from said forward end for biasing said jaws to a needle hub releasing position.

2. A needle holder according to claim 1 wherein said finger operable releasing means comprises a sleeve reciprocally mounted on said barrel and having at least one finger tab extending outward therefrom.

3. A needle holder according to claim 2 wherein said means for releaseably biasing said jaws to a needle hub releasing position comprises cam means carried by said sleeve.

4. A needle holder according to claim 1 wherein said segmented wall includes slots and said means for releasably biasing said jaws to a needle hub releasing position comprises cam means slidable axially along said slots between said jaws.

5. A needle holder according to claim 4 wherein said cam means is carried by a sleeve slideably mounted on said barrel.

6. A needle holder according to claim 1 wherein:

said segmented wall is divided by a plurality of slots into four segments; and said means for releasably biasing said jaws to a needle hub releasing position comprises cam means slidable axially along said slots between said jaws.

7. A needle holder according to claim 6 wherein said cam means is carried by a sleeve slideably mounted on said barrel.

8. A needle holder according to claim 7 wherein said sleeve is biased to a forwardmost position on said barrel.

9. A needle holder according to claim 8 wherein:

said segmented wall includes an outer end and an annular shoulder at said outer end thereof; and an elastic collar disposed around said segmented wall and said sleeve is biased against said annular shoulder by said elastic collar disposed around said socket.

10. A needle holder according to claim 9 wherein:

said sleeve is formed with a forward wall having an aperture through which said segmented wall extends; and said sleeve having a front end and a back end and includes a finger tab extending outward from each side thereof at said back end thereof.

11. A needle holder having a one hand detach needle hub connector assembly, comprising:

a generally cylindrical tubular barrel having an axis and a needle hub connector formed integral therewith on one end thereof;

said needle hub connector comprising a needle hub receiving socket defined by an annular axially extending wall having slots dividing said wall into segments defining a plurality of jaws having a forward end;

biasing means including annular shoulder mounted for axial movement on said jaws and including elastic means for normally biasing said annular shoulder toward said forward end for biasing said jaws into an innermost position for receiving and mounting a needle hub; and finger operable releasing means for biasing said annular shoulder await from said forward end for biasing said jaws to a needle releasing position.

12. A connector assembly according to claim 11 wherein said releasing means comprises cam means slidable axially along said slots between said jaws.

13. A needle holder according to claim 12 wherein said biasing means includes a sleeve and said cam means is mounted on said sleeve slideably mounted on said tubular barrel.

14. A needle holder according to claim 13 wherein said sleeve includes a finger tab extending outward from each side thereof.

15. A needle holder according to claim 14 wherein said sleeve is biased by an elastic collar toward forward position on said jaws.

16. A one hand releasable needle hub connector assembly, comprising:

an elongated generally cylindrical tubular barrel having a needle hub connector on one end;

said needle hub connector comprising necked down tubular axial extension of said tubular barrel defining an annular axially extending wall and a plurality of slots dividing said wall into segments defining a plurality of jaws having a forward end;

a finger operable sleeve mounted on said barrel and having an annular shoulder engaging sad jaws and elastic means biasing said sleeve toward said forward end for normally said jaws into an innermost position forming a socket for receiving and mounting a needle hub; and said finger operable sleeve including cam means and slideably mounted on said barrel away from said forward end for biasing said jaws to a needle releasing position.

17. A needle holder according to claim 16 wherein said wall is divided into four segments; and said cam means comprises wedges which extend into said slots between said segments of said wall.

18. A needle holder according to claim 17 wherein said sleeve includes a tab extending outward from opposite sides thereof.

19. A needle holder according to claim 18 wherein said elastic means biasing said sleeve toward said forward end is an elastic collar disposed around said extension.

20. A needle holder according to claim 19 wherein said wall segments are formed with guide means at said forward end.

* * * * *

UNITED STATES PATENT AND TRADEMARK OFFICE
CERTIFICATE OF CORRECTION

PATENT NO. : 5,693,028
DATED : December 2, 1997
INVENTOR(S) : Shillington

It is certified that error appears in the above-indentified patent and that said Letters Patent is hereby corrected as shown below:

Column 5, line 43, "await" should read --away--.

Signed and Sealed this

Fourteenth Day of April, 1998

Attest:

BRUCE LEHMAN

Attesting Officer

Commissioner of Patents and Trademarks